(12) United States Patent
Yi

(10) Patent No.: US 9,086,344 B2
(45) Date of Patent: Jul. 21, 2015

(54) ANTIQUE IDENTIFICATION METHOD

(71) Applicant: Weiqian Yi, Xiangtan (CN)

(72) Inventor: Weiqian Yi, Xiangtan (CN)

(*) Notice: Subject to any disclaimer, the term of this patent is extended or adjusted under 35 U.S.C. 154(b) by 0 days.

(21) Appl. No.: 14/178,270

(22) Filed: Feb. 11, 2014

(65) Prior Publication Data

US 2014/0233018 A1    Aug. 21, 2014

Related U.S. Application Data

(63) Continuation-in-part of application No. 13/589,430, filed on Aug. 20, 2012, now abandoned.

(60) Provisional application No. 61/490,003, filed on Aug. 22, 2011.

(51) Int. Cl.
*G01N 21/00* (2006.01)
*G01N 9/36* (2006.01)
*G02B 21/00* (2006.01)
*G01N 21/25* (2006.01)
*G01N 9/02* (2006.01)

(52) U.S. Cl.
CPC ............... *G01N 9/36* (2013.01); *G01N 21/25* (2013.01); *G02B 21/00* (2013.01); *G01N 2009/026* (2013.01)

(58) Field of Classification Search
CPC ... H01J 37/32935; G01N 21/64; G01N 21/68; G01N 2015/1037; G01J 3/02
USPC ........................................ 356/72–73
See application file for complete search history.

(56) References Cited

U.S. PATENT DOCUMENTS

2007/0020181 A1 *   1/2007   Workman et al. .............. 424/9.1

* cited by examiner

*Primary Examiner* — Abdullahi Nur
(74) *Attorney, Agent, or Firm* — Michael J. Foycik, Jr.

(57) ABSTRACT

A 4-in-1 antique identification method combines visual inspection, a colorimetric method, microscopic observation, and a density comparison method to form conclusions as to the date of an antique object. Among them the density comparison is to detect the identified object's unit weight, and compare it to known data of historical unit weights of objects, to determine the age of the object being measured. This combines the antique's inherent physical constant to confirm its age. This is repeated for each step, to provide a number of estimated age results for the object. If the results are in agreement, the result can be considered reliable and the object can be deemed authentic. This method especially applies to the identification of porcelain, jade and bronze with less equipment and easier operation.

1 Claim, 5 Drawing Sheets

ANTIQUE IDENTIFICATION METHOD

CROSS REFERENCE TO RELATED APPLICATIONS

Not applicable.

STATEMENT REGARDING FEDERALLY SPONSORED RESEARCH OR DEVELOPMENT

Not applicable.

FIELD OF THE INVENTION

The present invention relates to a method and apparatus for reliably identifying antique objects as either authentic or counterfeit, and particularly for identifying porcelain, jade and bronze objects.

BACKGROUND OF THE INVENTION

The present invention is in the technical field of Antique identification. More particularly, the present invention is in the technical field of antique identification/authentication methods.

An emphasis of the present invention relates to a method and apparatus for reliably identifying antique objects as either authentic or counterfeit, and particularly for identifying porcelain, jade and bronze objects.

Chinese antiques are prized by museums, art galleries, archaeologists and private collectors all over the world. More and more people buy and collect Chinese antiques not only because of their historical and cultural heritage value, but also economic value. The economic value is increasing significantly, so people greedy for profit have been encouraged to forge copies of old artwork and old crafted objects. Forgers employ modern scientific techniques to copy classic antiques, and their ingenious results can often pass for the real thing.

This situation creates a need for reliable authentication method to identify forgeries. Therefore, antique authentication methods are of increasing interest from all social classes. Visual inspection is the traditional identification method, and not only requires a vast knowledge but also many years of experience. Even so, such method can sometimes be fooled or blinded by modern technology used by counterfeiters, and so the collector or appraiser has been challenged on the reliability and accuracy of identification of antiques.

Scientific methods are available but not widely used due to either the relatively high cost involved or incomplete sample data or destruction to the object. For example, Thermoluminescence (TL) dating used in the authentication of old ceramic wares for the tests of trace of elements and fluorescent analysis, requires the removal of fairly large clay samples of approx. 3 mm diameter, which may destruct thin porcelain. And, the equipment and technological prowess may not be adequate in the face of advances in counterfeiting technology; the cost of instruments may be relatively high and the operators may not be sufficiently experienced or skilled at using such new instruments; a broad variety of samples collected from different places and times are required but the data accumulated are often incomplete and sometimes dubious; and forgers may invent new schemes in response to the new tests. Another method, radiocarbon dating, is only used for dating organic materials, but not applicable to inorganic materials such as porcelain.

SUMMARY OF THE INVENTION

The present invention is an antique identification method for users to solve the problems on authenticity, reliability and accuracy of antique identification under a standardized and scientific antique identification method. The antiques include porcelain, jade and bronze.

Furthermore, the present invention relates to a method and apparatus for reliably identifying antique objects as either authentic or counterfeit, and particularly for identifying porcelain, jade and bronze objects.

The present invention integrates four methods (steps) in one Method. The four methods (steps) are visual inspection, colorimetric method, microscopic observation and volume weight/density comparison. The results of using this Method are more accurate. The conclusions reached by this Method are likely to be trustworthy since the present invention combines the new scientific tests with traditional methods of authentication.

Furthermore, in an embodiment of the present invention, the method and apparatus further includes use of a computer, database, and program for input of data, analysis of data, comparison of data with known reference data stored in a memory of the computer, and provides an output indicating both the age and type of antique object and also the reliability of the identification.

DETAILED DESCRIPTION OF THE INVENTION

Figure 1:
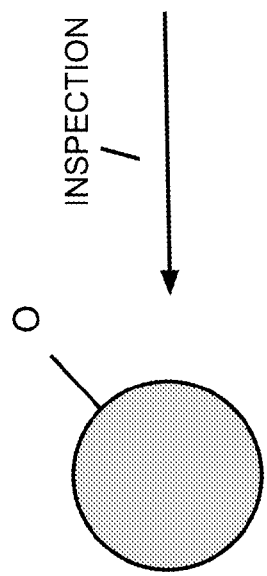
FIG. 1 is a schematic view of visual inspection of an object to be identified, which is a first step of the method according to the present invention.

Referring now to the invention in more detail, FIG. 1 is a schematic view of visual inspection (denoted by the labeled arrow) of an object O which is to be identified. This is a first step of the method according to the present invention, and is discussed further below.

Visual inspection is the first method (step) employed to date an object accurately. One must carefully examine the object's form, shape, craftsmanship, decoration and painting style, texture, physical composition, glaze color and texture, and ornamentation. In addition, one must always search for any kind of inscription, seal or mark written on the object.

As an example, there are many styles of vases which represent the different types used during different periods of history. An expert can tell the difference and so arrive at an estimated period of time if the antique is authentic. Likewise, there are many styles of jewelry, necklaces, bronze implements, and so on, which can be distinguished by an expert.

The visual inspection will also include study of the maker's marks, which vary greatly in time, place, and culture. Again, these aforementioned attributes are of importance to an expert.

Again, for the sake of emphasizing the types of attributes, these include: form, shape, craftsmanship, decoration and painting style, texture, physical composition, glaze color and texture, and ornamentation. An expert's opinion, when all these attributes are consistent with a specific age, can be indicative of authenticity. However, the reliability of this method will vary from person to person, and from one skill level to another, and additional steps are used according to the present invention as follows.

Figure 2:
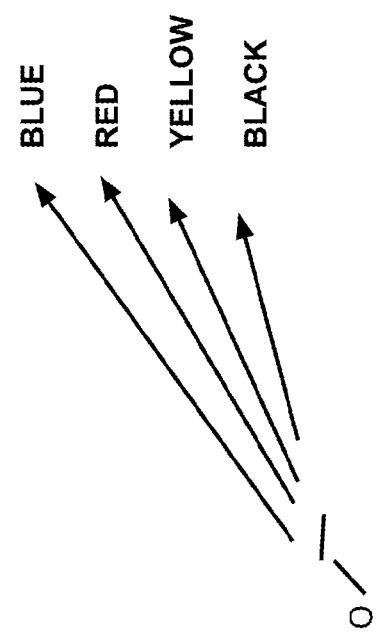
FIG. 2 is a schematic view of a colorimetric inspection of a portion of an object to be identified, which is a second step of the method according to the present invention.

FIG. 2 is a schematic view of a colorimetric inspection of a portion of the object O to be identified, which is a second step of the method according to the present invention. The colorimetric inspection uses known types of colorimetric analysis capable of resolving the spectrum of the object into specific values of saturation of the colors Blue, Red, Yellow, and Black. This is discussed in further detail below.

The Colorimetric method is the second method (step) of the present invention for dating an object accurately. The combination of blue, red, yellow and black can generate various colors. Each monochrome can be divided into ten sections from the lightest to the darkest, which can be shown as follows: 10 20 30 40 50 60 70 80 90 100, to correspondingly represent 10% to 100% of the saturation of the original color. The level (number) equal to zero means the saturation of the monochrome is 0%, namely white; whereas the level (number) equal to 100 means the saturation of the monochrome is 100%, namely the most saturated condition of the monochrome. These colors of each 10% of the color saturation from the lightest to the darkest forms a group of color code for color comparison, which is referred as color code, discussed below.

Objects from different periods of time have different glaze colors. The colorimetric method is to compare the object being test with known relevant contrast color codes, in order to identify the age. These known codes are in the form of a database.

The following is a list of glaze color codes/database (C—blue, M—red, Y—yellow, K—black), and exemplary known contrast codes which are typical of the database:

2.1. Tang dynasty white-glazed porcelain: C-10 M-10 Y-40 K-10
2.2. Tang polychrome "three-colors" (sancai) horse: yellow: C-0 M-60 Y-80 K-30; green: C-40 M-0 Y-60 K-30
2.3. Tang dynasty Jun porcelain: C-100 M-60 Y-30 K-10
2.4. Song dynasty Ru ware with greenish blue glaze: C-20 M-0 Y-20 K-30
2.5. Song dynasty Ru ware with sky blue glaze: C-40 M-0 Y-20 K-30
2.6. Song dynasty Song dynasty Ru ware with pale blue glaze: C-30 M-10 Y-20 K-20
2.7. Song dynasty Official (guan) ware with greenish blue glaze: C-0 M-0 Y-30 K-30
2.8. Song dynasty Official (guan) with greenish blue glaze: C-20 M-10 Y-30 K-30
2.9. Song dynasty Ge ware with cream glaze: C-20 M-30 Y-60 K-30
2.10. Song dynasty Ge ware with cream glaze: C-10 M-10 Y-30 K-10
2.11. Song dynasty ware of Jiaotanxia kiln: C-0 M-0 Y-10 K-5
2.12. Song dynasty ware of Xiuneisi kiln: C-5 M-10 Y-30 K-0
2.13. Song dynasty white glaze ware of Ding kiln: C-0 M-10 Y-20 K-10
2.14. Song dynasty white glaze ware of Ding kiln: C-10 M-10 Y-30 K-0
2.15. Song dynasty purple glaze ware of Ding kiln: C-0 M-60 Y-20 K-30
2.16. Song dynasty green glaze of Ding kiln: C-30 M-20 Y-60 K-60
2.17. Song dynasty purple glaze ware of Jun kiln: C-70 M-100 Y-40 K-0
2.18. Song dynasty celadon: C-20 M-0 Y-20 K-10
2.19. Song dynasty celadon: C-30 M-30 Y-40 K-10
2.20. Song dynasty Jun ware with light greenish blue glaze: C-30 M-0 Y-10 K-10
2.21. Porcelain of Longquan kiln: C-30 M-10 Y-30 K-0
2.22. Yuan dynasty red and green porcelain: C-0 M-20 Y-40 K-10
2.23. Early Yuan dynasty blue and white: C-100 M-80 Y-20 K-60
2.24. Yuan dynasty elegant blue and white: C-30 M-10 Y-10 K-30
2.25. Yuan dynasty Zhizheng type blue and white: C-100 M-60 Y-30 K-60
2.26. Yuan dynasty blue and white: C-100 M-80 Y-60 K-30
2.27. Ming dynasty Hongwu period underglaze red porcelain: C-10 M-40 Y-30 K-30
2.28. Ming dynasty Hongwu period blue and white porcelain: C-60 M-20 Y-10 K-60
2.29. Ming dynasty Yongle period blue and white: C-100 M-60 Y-20 K-60
2.30. Ming dynasty Xuande period wucai porceclain: red glaze C-0 M-60 Y-40 K-0
2.31. Ming dynasty Xuande period wucai porceclain: red: C-0 M-60 Y-40 K-10; yellow C-0 M-10 Y-60 K-10
2.32. Ming dynasty Xuande period red glaze porcelain: C-60 M-100 Y-100 K-0
2.33. Ming dynasty Xuande period blue and white polychrome (wucai):
C-0 M-60 Y-40 K-0
2.34. Ming dynasty Chenghua period doucai:
red: C-0 M-80 Y-30 K-10, green: C-80 M-0 Y-100 K-0
2.35. Ming dynasty Chenghua period doucai:
red C-10 M-80 Y-40 K-30, green: C-80 M-0 Y-60 K-30
2.36. Ming dynasty Chenghua period blue and white: C-70 M-10 Y-20 K-60
2.37. Ming dynasty Chenghua period red glaze porcelain: blue: C-10 M-60 Y-60 K-0
2.38. Ming dynasty Jiajing period blue glaze: C-80 M-5 Y-20 K-20
2.39. Ming dynasty Jiajing period blue and white porcelain: C-100 M-80 Y-30 K-30
2.40. Ming dynasty Wanli period polychrome (wucai) porcelain:
yellow: C-20 M-30 Y-60 K-10, green: C-70 M-40 Y-60 K-10
2.41. Qing dynasty Kangxi period blue and white: C-100 M-60 Y-20 K-30
2.42. Qing dynasty Kangxi period blue and white and sancai: C-0 M-60 Y-60 K-10
2.43. Qing dynasty Kangxi period blue and white: blue: C-100 M-80 Y-10 K-0
2.44. Qing dynasty Kangxi period blue and white: C-80 M-30 Y-20 K-10
2.45. Qing dynasty Yongzheng period blue and white: C-100 M-60 Y-20 K-300
2.46. Qing dynasty Yongzheng period doucai:
C-70 M-20 Y-40 K-10; yellow: C-0 M-20 Y-80 K-10
2.47. Qing dynasty Qianlong period Big arrow holder:
red: C-0 M-100 Y-60 K-10; green: C-60 M-0 Y-40 K-10.
2.48. Qing dynasty Qianlong period famille rose vase:
brown: C-40 M-60 Y-80 K-50; red: C-10 M-60 Y-60 K-10

2.49. Qing dynasty Qianlong period famille rose bowl on white ground:
red: C-10 M-40 Y-10 K-10; green: C-50 M-0 Y-30 K-30
2.50. Qing dynasty Qianlong period copper-red glaze:
red: C-10 M-80 Y-30 K-10; green: C-60 M-10 Y-60 K-10
2.51. Qing dynasty Daoguang period famille rose vase:
red: C-40 M-100 Y-100 K-0; yellow: C-20 M-0 Y-80 K-0
2.52. Qing dynasty Guangxu period blue and white doucai:
blue and white: C-70 M-20 Y-0 K-30; red: C-30 M-80 Y-100 K-10
2.53. Blue and white fahuacai:
green: C-50 M-0 Y-30 K-60; red: C-0 M-60 Y-10 K-30; blue and white: C-90 M-100 Y-20 K-0
2.54. Dehua white porcelain: C-5 M-5 Y-0 K-0
2.55. Modern Chinese red: M-100 Y-100

Microscopic observation (not shown in the drawings) is the third method (step) to date an object O accurately. This is not shown since microscopy itself is very well known. This method is to apply the magnifier or microscope on the object's microscopic features of under glaze structure, bubble formation, rust color, soil penetration and crystallization, etc.

In practice, the microscopic examination is performed at a 200× magnification, and is compared with a database of known specimens. These images typically include patterns of spots, colors, lines, curves, and inclusions of various types. By matching the object's patterns with the known database, it is possible to form an opinion of the object's age based on the matching patterns.

Figure 3:
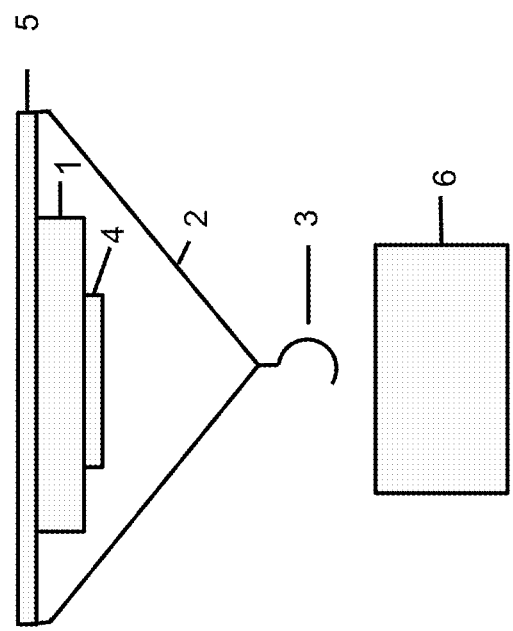
FIG. 3 is a schematic view of an apparatus for determining volume weight/density values of an object to be identified, which is a fourth step of the method according to the present invention.

FIG. 3 is a schematic side view of an apparatus for determining volume weight/density values of an object O to be identified, which is a fourth step of the method according to the present invention. FIG. 3 shows a digital scale 1, a hanging rope 2 supporting a hook 3, an iron supporting rod 5 which supports the hanging rope 2 and which overlies the digital scale 1, and a supporting plate 4 for supporting the digital scale 1. A water bucket 6 is shown for immersion of the object O in water.

The digital scale 1 is placed on supporting plate 4, the iron supporting rod 5 is above the digital scale 1 and ties the hanging rope 2 at the ends of the iron support rod 5, and sets the hook 3 for holding the object O in the water bucket 6. This type of apparatus takes two measurements of weight, one when the object O is not in the bucket 6, and the second measurement when the object O is immersed in the water in the bucket.

These two measurements can be used to determine specific gravity, also called relative density, and is very well documented in the scientific literature, and can be found also in a Wikipedia article for relative density and for hydrostatic weighing. The specific gravity can then be compared with a table of known specific gravities for known antiques, to determine whether it is consistent with the other results from the other steps of the present invention.

Thus, the device of FIG. 3 is used in performing step four of the present invention. The above step 4 describes the measurement of volume weight/density E: first, use the digital scale to weight the object O to get an object weight G (unit: gram), then to fully cover the object in water and weight the object again to get a weight G1 (unit: gram) while it's in stationary state under the water, by formula:

$$E = G/(G-G1).$$

The following is an exemplary listing of known values for differing types of historical antiques. List of volume weight/density (unit: g/cm³)

| | |
|---|---|
| 4.1. Tang dynasty blue and white bowl | 2.14 |
| 4.2. Tang dynasty blue and white wine vessel | 2.21 |
| 4.3. Tang sancai horse | 2.08 |
| 4.4. Southern Song dynasty Ru ware washer | 2.00 |
| 4.5. Southern Song dynasty Ru ware wine vessel | 2.14 |
| 4.6. Song dynasty secret color porcelain pot | 2.20 |
| 4.7. Song dynasty Jun ware | 2.14 |
| 4.8. Song dynasty Ge ware water jet | 2.14 |
| 4.9. Jian ware black cup | 2.21 |
| 4.10. Baiding bowl | 2.25 |
| 4.11. Jun ware purple tassie | 2.25 |
| 4.12. Yaozhou ware vase | 2.20 |
| 4.13. Longquan ware vase | 2.19 |
| 4.14. Cizhou ware pot | 2.20 |
| 4.15. Black Jian ware golden thread cup | 1.89 |
| 4.16. Yuan dynasty underglaze red plum vase | 2.10 |
| 4.17. Yuan dynasty blue and white plum vase | 2.10 |
| 4.18. Yuan dynasty imitation of official (guan) porcelain bowl | 2.24 |
| 4.19. Yuan dynasty red glaze vase | 2.06 |
| 4.20. Yuan dynasty Ge ware bowl | 2.24 |
| 4.21. Ming dynasty Hongwu period flat pot | 2.23 |
| 4.22. Ming dynasty Yongle period blue and white | 2.28 |
| 4.23. Ming dynasty Xuande period blue and white box | 2.04 |
| 4.24. Ming dynasty Xuande period plate | 2.22 |
| 4.25. Ming dynasty Wanli period blue and white | 2.14 |
| 4.26. Ming dynasty Jiajing period blue and white | 2.20 |
| 4.27. Ming dynasty Chenghua period doucai bowl | 2.25 |
| 4.28. Ming dynasty Chenghua period teacup | 2.20 |
| 4.29. Ming dynasty wine vessel | 1.82 |
| 4.30. Ming dynasty blue and white burner | 2.22 |
| 4.31. Xing ware white porcelain pot | 2.17 |
| 4.32. Blown glaze pot with character mark of "shou" | 2.00 |
| 4.33. Qing dynasty Kangxi period blue and white bowl | 2.10 |
| 4.34. Qing dynasty Kangxi period blue and white teacup | 2.10 |
| 4.35. Qing dynasty Kangxi period inkpad box | 2.28 |
| 4.36. Qing dynasty Yongzheng period doucai | 2.23 |
| 4.37. Qing dynasty Yongzheng period bowl | 2.25 |
| 4.38. Qing dynasty Yongzheng period enamel | 2.10 |
| 4.39. Qing dynasty Qianlong period enamel | 2.25 |
| 4.40. Qing dynasty Qianlong period burner | 2.28 |
| 4.41. Qing dynasty Qianlong period guyuexuan vase | 2.24 |
| 4.42. Qing dynasty Qianlong period flower bowel | 2.23 |
| 4.43. Qing dynasty Qianlong period famille rose (fencai) teacup | 2.26 |
| 4.44. Qing dynasty Qianlong period sacrificial red | 2.17 |
| 4.45. Qing dynasty Qianlong period fencai | 2.25 |
| 4.46. Qing dynasty Qianlong period jar | 2.23 |
| 4.47. Qing dynasty Guangxu period drinking cup | 2.29 |
| 4.48. Qing dynasty Guangxu period blue and white doucai | 2.29 |
| 4.49. Cowpea red | 2.22 |
| 4.50. Porcelain of the Republic of China | 2.31-2.35 |
| 4.51. Modern blue and white | 2.40 |
| 4.52. Copy of imperial porcelain | 2.30 |
| 4.53. Copy of Ru ware washer | 2.38 |
| 4.54. Copy of Qianlong period porcelain | 2.32 |
| 4.55. Copy of Yongzheng period porcelain | 2.33 |
| 4.56. Copy of porcelain vase with eight peach design | 2.37 |
| 4.57. Copy of greenish blue vase | 2.35 |
| 4.58. Copy of Xuande period blue and white | 2.40 |
| 4.59. Copy of Yongzheng period porcelain | 2.33 |
| 4.60. Copy of Hongwu period water bowl | 2.40 |

Figure 4:
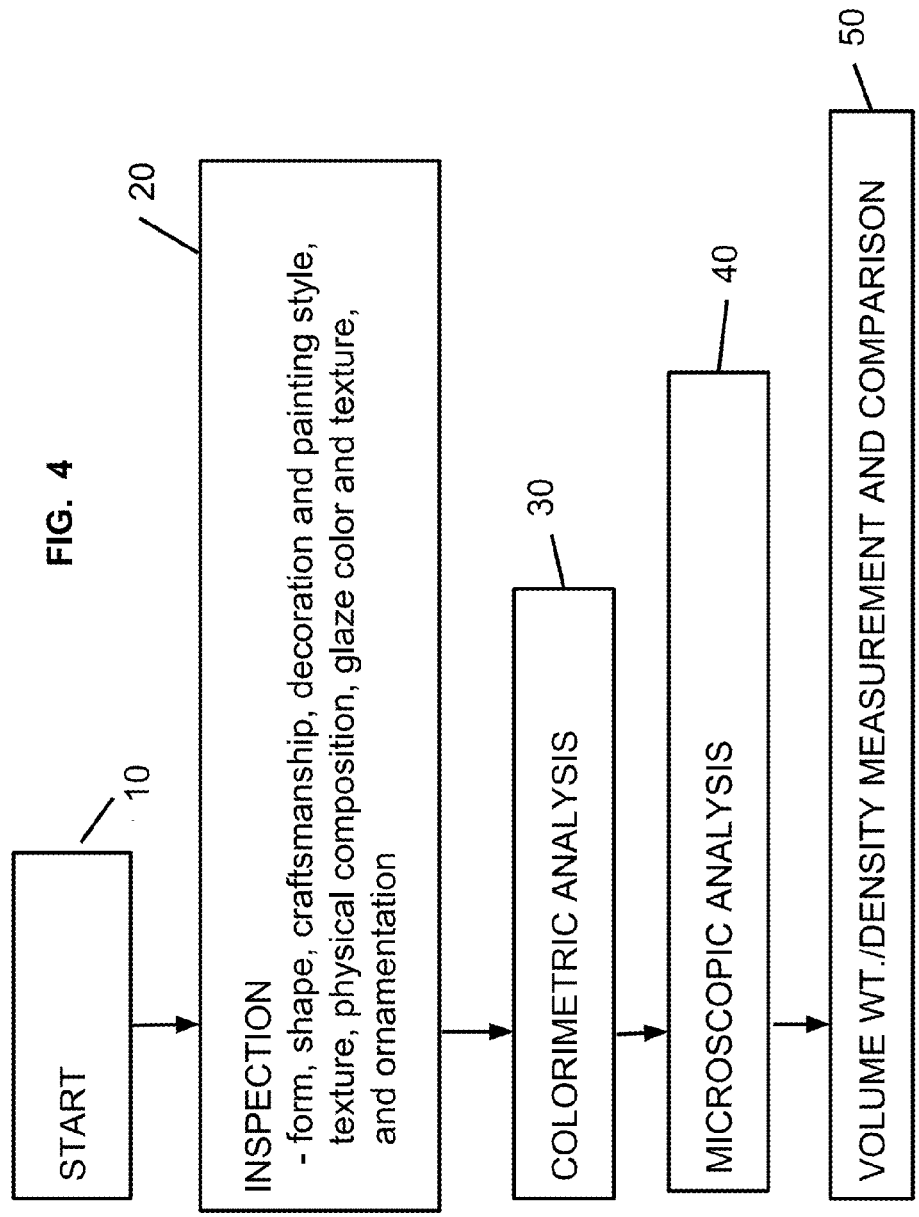
FIG. 4 is a flowchart which schematically depicts the four steps of the method according to the present invention.

FIG. 4 is a flowchart which schematically depicts the steps of the method according to the present invention. The authentication starts at the START step 10, followed by an INSPECTION step 20, a COLORIMETRIC ANALYSIS step 30, a MICROSCOPIC ANALYSIS step 40, and a VOLUME WT./DENSITY MEASUREMENT AND COMPARISON step 50. Each of the foregoing steps has been discussed in detail in the foregoing discussion.

When the four steps result in a consistent date of the object O, then the determination can be considered to be very reliable and the object can be deemed to be authentic.

However, if the four steps result in completely inconsistent results for the date of the object O, then the object O can be deemed to be a counterfeit object.

The advantages of the method of FIG. 4 of the present invention includes, without limitation, that it minimizes the uncertainty of human factors in antique identification which supplies a reliable and standard antique authentication method; that it is cost effective and non-destructive; it uses simple equipment and is easy to operate, so the identification could be done at home.

Figure 5:
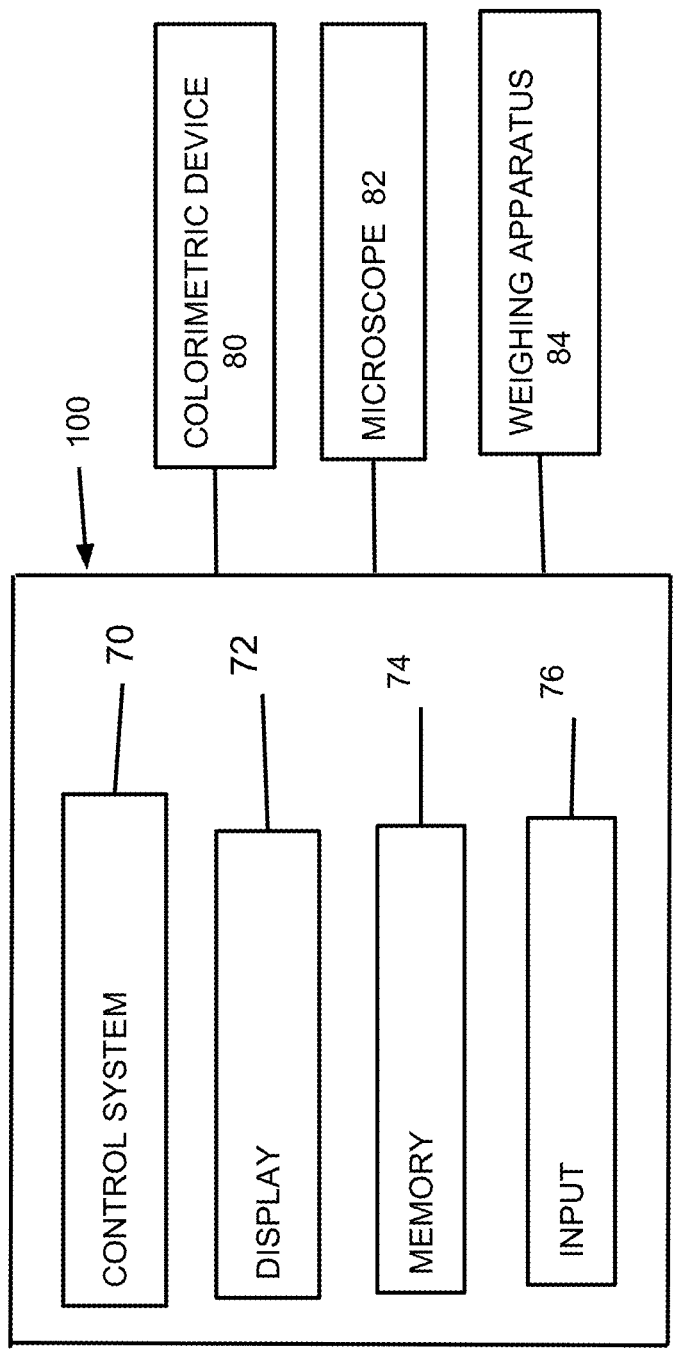
FIG. 5 is a schematic view of a further embodiment including an apparatus using a computer system, for use in conducting various ones of the steps of the method shown in FIG. 4.

FIG. 5 is a schematic view of a further embodiment including an apparatus using a computer system 100, for use in conducting steps like those of the method shown in FIG. 4. The computer 100 includes a control system 70, a display 72, a memory 74, and an input 76. These elements of a computer are well known, and all known variations thereof are contemplated as being within the scope of the present invention.

The computer 100 is used in connection with a colorimetric device 80, a microscope 82, and a weighing apparatus 84 similar to that of FIG. 3. Colorimetric devices are known, and any suitable known type is contemplated as being usable in the present invention.

In use, the memory 74 stores the database information referred to hereinabove. The control system 70 includes a processor and can process the input information, find correlations between the input information and the database using known types of programming methods. For example, pattern recognition software is well known, and can be used to match input microscopic slides with reference samples having similar features, color, and elements.

Likewise, indicia can be searched and matched, colors searched and matched, and specific densities searched and matched. The results are displayed by the display 72.

Figure 6:
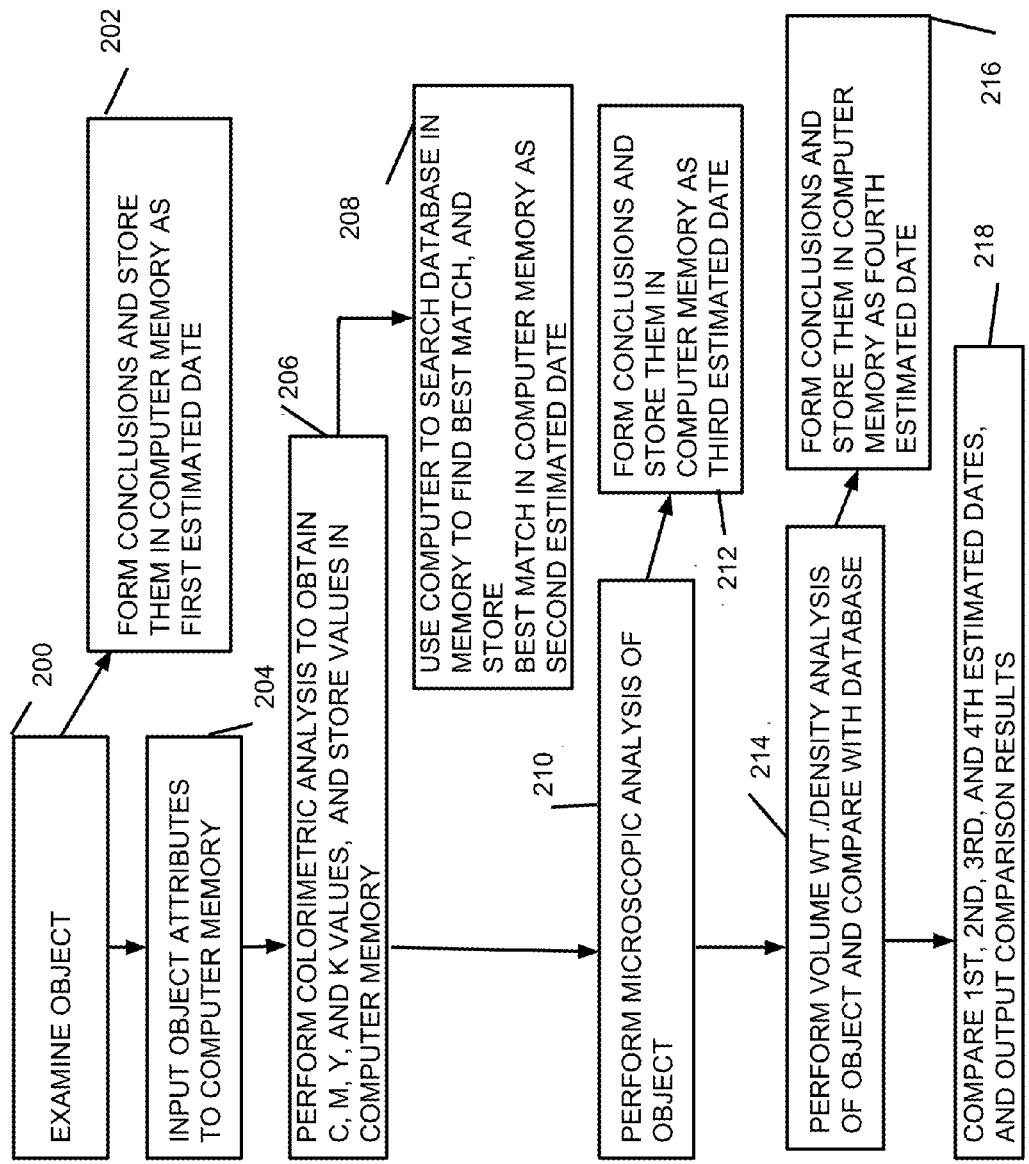
FIG. 6 is a flowchart which schematically depicts further embodiment of FIG. 5 including an apparatus using a computer system, for conducting various steps in antique identification.

FIG. 6 is a flowchart which schematically depicts use of the further embodiment of FIG. 5, which includes the apparatus using the computer system 100, for conducting various steps in antique identification as follows.

The flowchart of FIG. 6 starts at step 100 where the object O is examined by an expert examiner. At step 202, the examiner forms conclusions and at step 204 the examiner inputs the object attributes (discussed hereinabove) into the computer 100 which stores them in the computer memory 74. In step 202, the conclusions are stored as a first estimated date.

The next step of the method follows at step 206, which is to perform the colorimetric analysis to obtain C, M, Y, and K values (as discussed hereinabove), and stores those values in the computer memory 74. The computer 100 is used at step 208 to search the relevant database stored in the computer memory 74 to find a best match and to store the best match in computer memory representing a second estimated date.

The next step of the method follows at step 210, which is to perform the microscopic analysis of the object O, in the manner already discussed hereinabove. This microscopic analysis is used, in conjunction with comparison with a reference library of stored historical objects/data as discussed hereinabove, to form conclusions and store them in the computer memory as a third estimated date.

The following step of the method is at step 214, which is to use the apparatus of FIG. 3 as discussed hereinabove to perform a volume weight/density analysis of the object O and compare it with a database stored in the computer memory 74.

At step 216, the computer 100 forms conclusions as a result of the comparison in order to find a match and use its date. That date is stored in the computer memory 74 as a fourth estimated date.

At step 218, the first, second, third, and fourth estimated dates are compared, and the results are output by the computer. If the results are in close agreement, then the object O is assigned a date with a high reliability, and the object O can be judged to be authentic. If the results are not in agreement, then the object O can be judged as not authentic, or as not having a reliable date, and can thus be deemed a counterfeit.

For example, in a low-level type of forgery all four dates might be different. In the case of a high-level forgery, two or three of the results may be in agreement but not the fourth. It would be exceedingly difficult to match all fourth methods for form a counterfeit, and therefore the results can be considered highly reliable and objective.

The foregoing written description of the invention enables one of ordinary skill to use what is considered presently to be the best method.

The invention being thus described, it will be evident that the same may be varied in many ways by a routineer in the applicable arts. Such variations are not to be regarded as a departure from the spirit and scope of the invention and all such modifications are intended to be included within the scope of the claims.

What is claimed is:

1. An apparatus for reliably identifying antique crafted objects as either authentic or counterfeit by estimating the date thereof, the object being an artwork or a crafted object made from ceramic, jade, or bronze, comprising: a computer system having a display, an input, a memory, and a control system; said memory containing stored known color data, stored known reference microscopic data, and stored known reference density data; a colorimetric device for analyzing the object to produce color data pertaining to the object; and wherein said computer system is used for comparing said stored known reference color data with said color data pertaining to the object to obtain an estimated age; a microscope apparatus for forming a microscopic image of the object, and wherein said computer system is used for comparing said microscopic image of the object to said stored known reference microscopic image data to obtain an estimated age; and a weighing apparatus for determining volume weight/density data about the object, and wherein said computer system is used for comparing said volume weight/density data to said stored known reference density data to obtain an estimated age; said computer system performing a comparison of the estimated ages determined by said calorimetric device, said microscope apparatus, and said weighing apparatus to produce an output indicating consensus or non-consensus, whereby consensus agreement of said estimated ages indicates an authentic object and non-consensus indicates a counterfeit object.

* * * * *